(12) United States Patent
Van Niekerk et al.

(10) Patent No.: US 12,727,937 B2
(45) Date of Patent: Sep. 8, 2026

(54) ABLATION AND MAPPING WITH A SINGULAR MULTI-ELECTRODE CATHETER

(71) Applicant: Biosense Webster (Israel) Ltd., Yokneam (IL)

(72) Inventors: Pieter Van Niekerk, Monrovia, CA (US); Jamie Henriquez, Pasadena, CA (US); Cesar Fuentes-Ortega, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 896 days.

(21) Appl. No.: 17/570,829

(22) Filed: Jan. 7, 2022

(65) Prior Publication Data

US 2023/0009573 A1 Jan. 12, 2023

Related U.S. Application Data

(60) Provisional application No. 63/220,269, filed on Jul. 9, 2021.

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00577* (2013.01);
(Continued)

(58) Field of Classification Search
CPC . A61B 18/1492; A61B 18/1206; A61B 18/14; A61B 18/12; A61B 2018/00577;
(Continued)

(56) References Cited

U.S. PATENT DOCUMENTS 6,023,638 A * 2/2000 Swanson .............. A61B 5/6855 606/41
6,987,995 B2 1/2006 Drysen
(Continued)

FOREIGN PATENT DOCUMENTS

JP 2002143178 A 5/2002
JP 2008521504 A 6/2008
(Continued)

OTHER PUBLICATIONS

Extended European Search Report and Opinion dated Aug. 1, 2022, from corresponding European Application No. 22155876.0.
(Continued)

*Primary Examiner* — Beverly M Flanagan
*Assistant Examiner* — Abigail M Ziegler

(57) ABSTRACT

An adapter can include circuitry that can toggle between a mapping state and an ablation state. In the mapping state the circuitry can connect the catheter to a mapping system so that the catheter can measure electrical signals from multiple independent electrodes on an end effector of the catheter. In the ablation state the circuitry can connect the catheter to an ablation generator so that the catheter can apply electrical signals to the electrodes to ablate using IRE and/or RF techniques. The circuitry can short together a group of electrodes in the ablation state and electrically isolate the electrodes in that group from each other when in the mapping state. Using the adapter, the catheter can ablate and map at a treatment site without having to be repositioned between the mapping and ablation steps.

12 Claims, 9 Drawing Sheets

(52) U.S. Cl.
CPC ............... *A61B 2018/00613* (2013.01); *A61B 2018/00642* (2013.01)

(58) Field of Classification Search
CPC ........... A61B 2018/00613; A61B 2018/00642; A61B 2018/00351; A61B 2018/00839; A61B 5/283; A61B 5/367
See application file for complete search history.

(56) References Cited

U.S. PATENT DOCUMENTS

| | | | | |
|---|---|---|---|---|
| 7,228,164 | B2 | 6/2007 | Fuimaono et al. | |
| 2011/0319948 | A1* | 12/2011 | Onodera | A61N 1/0563 607/5 |
| 2018/0214202 | A1* | 8/2018 | Howard | A61B 5/6852 |
| 2018/0221085 | A1 | 8/2018 | Blanck et al. | |
| 2019/0192208 | A1* | 6/2019 | Harmouche | A61B 18/02 |
| 2020/0206461 | A1 | 7/2020 | Govari et al. | |
| 2021/0161592 | A1 | 6/2021 | Altmann et al. | |
| 2021/0169550 | A1 | 6/2021 | Govari et al. | |
| 2021/0169567 | A1 | 6/2021 | Govari et al. | |
| 2021/0169568 | A1 | 6/2021 | Govari et al. | |
| 2021/0177503 | A1 | 6/2021 | Altmann et al. | |
| 2021/0186604 | A1 | 6/2021 | Altmann et al. | |
| 2021/0191642 | A1 | 6/2021 | Yu et al. | |
| 2021/0196372 | A1 | 7/2021 | Altmann et al. | |
| 2021/0369132 | A1 | 12/2021 | Van Niekerk et al. | |
| 2022/0202484 | A1* | 6/2022 | Wang | A61B 18/12 |
| 2023/0009573 | A1 | 1/2023 | Van Niekerk et al. | |

FOREIGN PATENT DOCUMENTS

| | | | |
|---|---|---|---|
| JP | 2020518335 | A | 6/2020 |
| JP | 2021087778 | A | 6/2021 |
| JP | 2023509387 | A | 3/2023 |
| WO | 2021127558 | A1 | 6/2021 |

OTHER PUBLICATIONS

Search Report dated Jun. 26, 2025, from corresponding Japanese application 2022-018534.
Notice of Reasons for Refusal dated Jul. 1, 2025, from corresponding Japanese application 2022-018534.
Written Opinion for Refusal dated Sep. 11, 2025, from corresponding Japanese application 2022-018534.
Notice of Reasons for Refusal dated Nov. 18, 2025, from corresponding Japanese application 2022-018534.

* cited by examiner

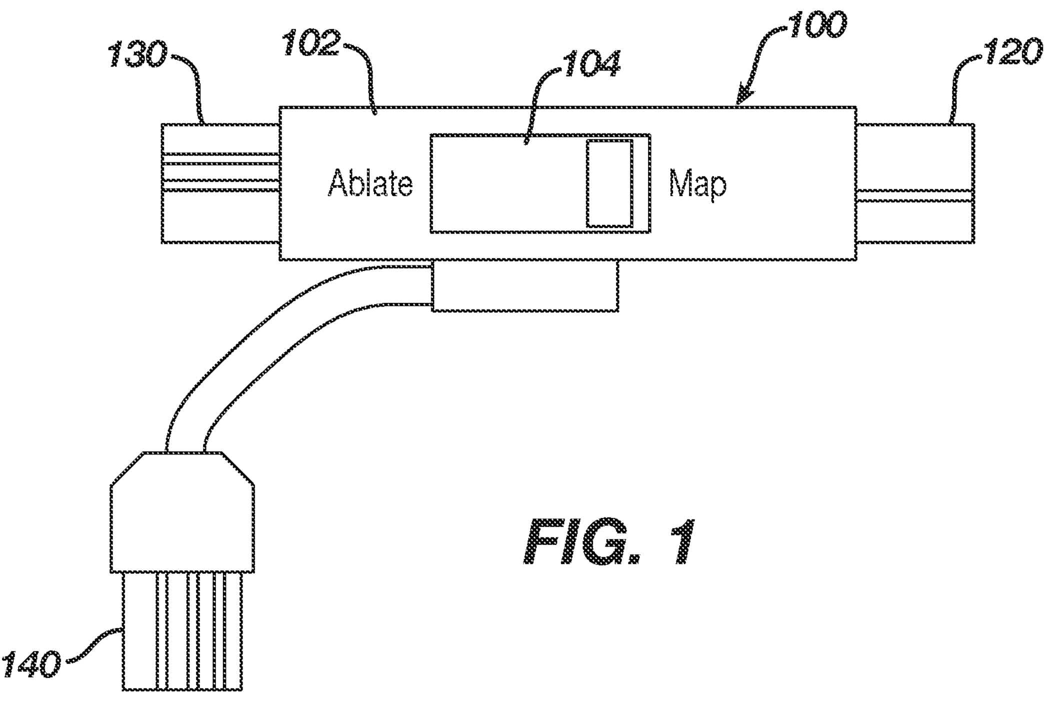
FIG. 1
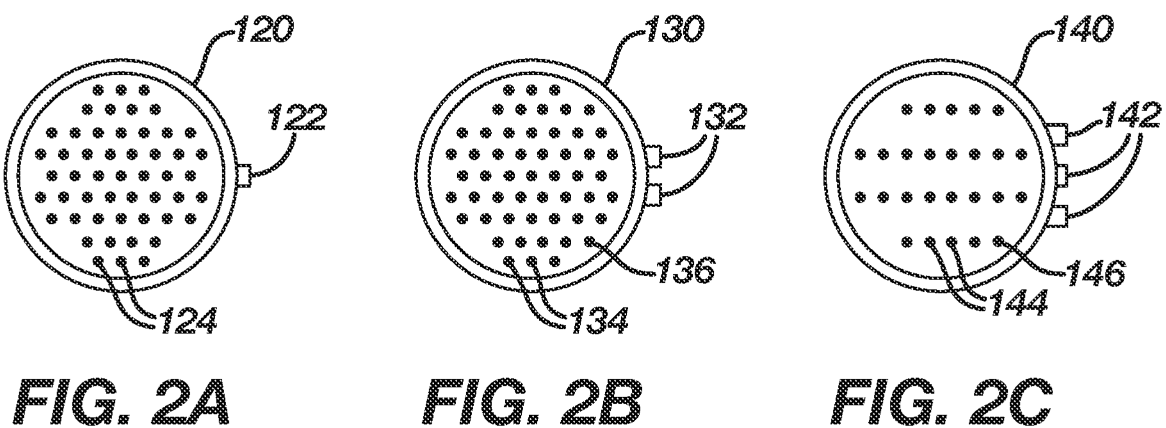
FIG. 2A
FIG. 2B
FIG. 2C

ABLATION AND MAPPING WITH A SINGULAR MULTI-ELECTRODE CATHETER

CROSS REFERENCE TO RELATED APPLICATION

The present application claims benefit of priority to U.S. Provisional Patent Application No. 63/220,269 filed Jul. 9, 2021. The entire contents of which are hereby incorporated by reference.

FIELD

The present invention relates to an apparatus for facilitating performing intravascular ablation and mapping with a singular multi-electrode catheter and related methods.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Sources of undesired signals are typically located in tissue of the atria a ventricle. Regardless of source, unwanted signals are conducted elsewhere through heart tissue where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is possible to cease or modify the propagation of unwanted electrical signals from one portion of the heart to another. The ablation process destroys the unwanted electrical pathways by formation of non-conducting lesions.

Such procedures therefore typically include a two-step process: (1) mapping; and (2) ablation. During mapping, a catheter having an end effector with a high density of electrodes is moved across target tissue, electrical signals are acquired from each electrode, and a map is generated based on the acquired signals. During ablation, lesions are formed at regions selected based on the map to disrupt electrical signals through those regions. Presently the most common ablation technique involves applying radio frequency (RF) electrical signals via electrodes to tissue to generate heat. Irreversible electroporation (IRE) ablation is a more recently developed technique which involves applying short duration high voltage pulses across tissue to cause cell death. Differing objectives of the ablation and mapping steps results in differing catheter design goals, and therefore ablation and mapping are typically performed using different catheters.

SUMMARY

An adapter and method of using the same are presented herein which can be used to perform mapping and ablation with a singular catheter. The adapter can include circuitry that can toggle between a mapping state and an ablation state. The catheter can measure electrical signals from multiple independent electrodes on an end effector of the catheter when the circuitry is in the mapping state. The catheter can apply electrical signals to the multiple electrodes to ablate when the circuitry is in the ablation state. The circuitry can switch electrodes of the end effector between being connected to a mapping system and being connected to an ablation generator. The circuitry can short together a group of electrodes in the ablation state and electrically isolate the electrodes in that group from each other when in the mapping state. The shorted electrodes in the group can collectively provide a surface area large enough to facilitate ablation using IRE and/or RF techniques. Using the adapter, the catheter can ablate and map at a treatment site without having to be repositioned between the mapping and ablation steps.

An example adapter includes a first plurality of contacts, a second plurality of contacts, a third plurality of contacts, and circuitry configured to toggle between a mapping state and an ablation state. The first plurality of contacts are configured to electrically connect with electrodes of a multi-electrode catheter. The second plurality of contacts are configured to electrically connect with a catheter mapping system. The third plurality of contacts are configured to electrically connect with an ablation generator. The first plurality of contacts are in electrical communication with the second plurality of contacts in the mapping state. The first plurality of contacts are in electrical communication with the third plurality of contacts in the ablation state.

When the circuitry is in the mapping state, first and second contacts of the first plurality of contacts can be electrically isolated from each other. When the circuitry is in the ablation state, the first and second contacts can be electrically shorted to each other. The first contact and the second contact can be configured to respectively electrically connect to a first electrode and a second electrode on a common spine of the catheter. Alternatively, the first contact and the second contact can be configured to respectively electrically connect to a first electrode on a first spine of the catheter and a second electrode on a second spine of the catheter distinct from the first spine. When the circuitry is in the ablation state, the first and second contacts can be electrically shorted to additional contacts of the first plurality of contacts such that the circuitry is configured to short a circular constellation of electrodes of the catheter.

When the circuitry is in the mapping state, each contact of the first plurality of contacts can be electrically isolated from each other, and when the circuitry is in the ablation state, a first portion of the first plurality of contacts can be electrically shorted to each other, a second portion of the first plurality of contacts can be electrically shorted to each other, and the first portion can be electrically isolated from the second portion. The first portion can be configured to electrically contact electrodes on a first spine of the catheter. The second portion can be configured to electrically contact electrodes on a second spine of the catheter distinct from the first spine.

When the circuitry is in the ablation state, the circuitry can be configured to transmit RF electrical energy from the third plurality of contacts to the first plurality of contacts to thereby enable thermal ablation by at least a portion of the electrodes of the catheter. Additionally, or alternatively, when the circuitry is in the ablation state, the circuitry can be configured to transmit voltage pulses from the third plurality of contacts to the first plurality of contacts to thereby enable irreversible electroporation ablation by at least a portion of the electrodes of the catheter.

When the circuitry is in the ablation state, a portion of the first plurality of contacts can be shorted to result in at least a minimum electrode surface area required for irreversible electroporation ablation. The minimum electrode surface area can include one or more electrodes electrically connected to each other so that the one or more electrodes combine to provide a large surface area electrode for ablation.

The adapter can further include a user interface configured to toggle the circuitry between the mapping state and the ablation state. The user interface can include a mechanical switch.

The adapter can further include a first connector, a second connector, a third connector, and a portable adapter body providing structural support for the first, second, and third connectors. The first connector can house the first plurality of contacts and can be configured to mate with the catheter. The second connector can house the second plurality of contacts and can be configured to mate with the catheter mapping system. The third connector can house the third plurality of contacts and can be configured to mate with ablation generator.

The adapter can further include a communication system configured to receive instructions from an external computing device. The communication system can be supported by the portable adapter body. The external computing device can be external to the adapter body. The circuitry can be configured to toggle between the mapping state and the ablation state in response to instructions received by the communication system from the external computing device.

An example method of treating cardiac arrhythmia can include one or more of the following steps which can be executed in a variety of sequences and together with additional steps as understood by a person skilled in the pertinent art according to the teachings herein. The method can include positioning electrodes of a multi-electrode catheter against tissue of a heart in a first orientation, measuring electrical potentials of the electrodes and thereby of the tissue while the electrodes are in the first orientation, and while maintaining the position of the electrodes in the first orientation, ablating the tissue via the electrodes.

The method can include measuring electrical potentials of additional electrodes of the multi-electrode catheter. The method can include deactivating the additional electrodes while ablating the tissue.

Measuring electrical potentials of the electrodes can include measuring electrical potentials between first and second electrodes. Ablating the tissue can include synchronously applying an electrical signal to ablate the tissue to the first and second electrodes. The method can include positioning the first and second electrodes such that the first and second electrodes are on a common spine of the catheter. The method can include positioning the first and second electrodes such that the first electrode is on a first spine of the catheter and the second electrode is on a second spine of the catheter distinct from the first spine.

Ablating the tissue via the electrodes can include ablating a circular area of tissue by the electrodes.

Measuring electrical potentials of the electrodes can include measuring a distinct electrical potential at each of the electrodes. Ablating the tissue can include applying a first electrical signal to a first portion of the electrodes that are electrically shorted to each other and applying a second electrical signal distinct from the first electrical signal to a second portion of the electrodes that are electrically shorted to each other.

The method can include ablating tissue via the first portion of the electrodes being disposed on a first spine of the catheter. The method can include ablating tissue via the second portion of the electrodes being disposed on a second spine of the catheter distinct from the first spine.

The method can include applying radio frequency (RF) electrical energy from the electrodes to the tissue thereby thermally ablating the tissue.

The method can include applying voltage pulses to the electrodes thereby ablating the tissue with irreversible electroporation. The method can include applying voltage pulses to the electrodes such that a cumulative electrode surface area of the electrodes is at least a minimum electrode surface area required for irreversible electroporation ablation.

The method can include toggling, via a user interface, the electrodes of the multi-electrode catheter between a mapping state and an ablation state, such that in the mapping state the electrodes are in electrical communication with a mapping system configured to measure the electrical potentials of the electrodes and in the ablation state the electrodes are in electrical communication with an ablation generator configured to ablate the tissue via the electrodes. Toggling the electrodes via the user interface can include moving a mechanical switch.

The method can include joining a first connector of an adapter to the catheter such that the electrodes are in electrical communication with a first plurality of contacts of the first connector. The method can include joining a second connector of the adapter to a mapping system configured to measure the electrical potentials of the electrodes. The method can include joining a third connector of the adapter to an ablation generator configured to ablate the tissue via the electrodes.

The method can include transmitting instructions from an external computing system to the adapter to cause the catheter to toggle between measuring electrical potentials of the electrodes and ablating the tissue via the electrodes, the external computing system being external to a portable body of the adapter.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is an illustration of an example adapter according to aspects of the present invention.

FIGS. 2A, 2B, and 2C are illustrations of a catheter connector, a mapping system connector, and an ablation generator connector respectively according to aspects of the present invention.

DETAILED DESCRIPTION

Figure 3:
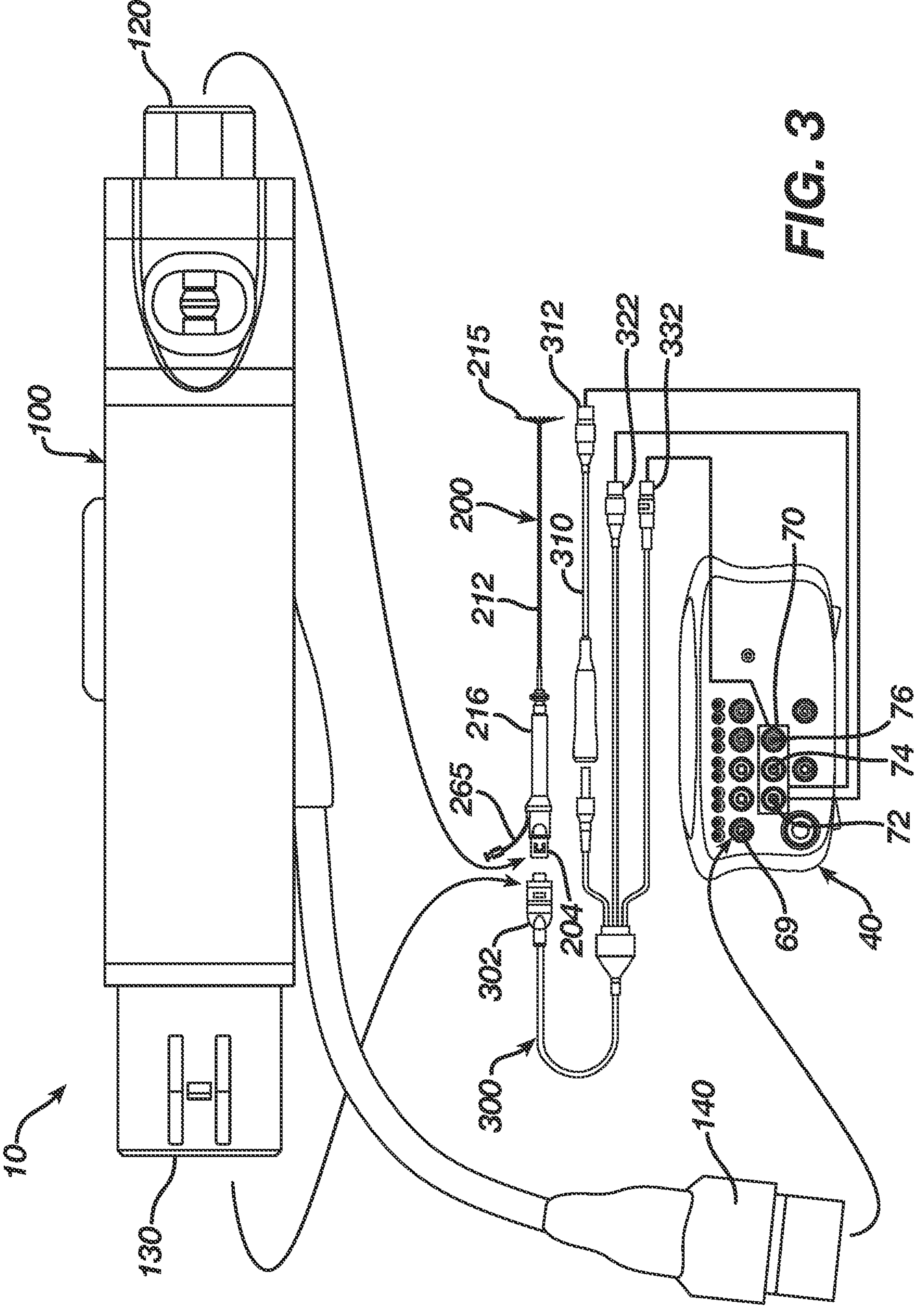
FIG. 3 is an illustration of an example system configured to map and ablate with a singular catheter according to aspects of the present invention.

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which includes by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Teachings, expressions, versions, examples, etc. described herein may be combined with other teachings, expressions, versions, examples, etc. that are described herein, including those examples provided in the references attached in the Appendix of U.S. Provisional Patent Application No. 63/220,269, to which the present application claims priority. The following-described teachings, expressions, versions, examples, etc. should therefore not be viewed in isolation relative to each other. Various suitable ways in which the teachings herein may be combined are apparent to those skilled in the pertinent art in view of the teachings herein. Such modifications and variations are intended to be included within the scope of the claims.

Examples included herein generally include circuitry that can cause a catheter to function both as mapping catheter and an ablation catheter. Because of the competing objectives of mapping and ablation, currently a mapping catheter is used to determine aberrant signals, the mapping catheter is removed, and an ablation catheter is positioned to disrupt the aberrant signals measured by the mapping catheter. Sophisticated computer-generated images are used by a physician to guide the ablation catheter to the correct location. A catheter which can perform both mapping and ablation can eliminate the need to guide a second, ablation catheter to the aberrant signals. By using the same catheter for both mapping and ablation, once an aberrant tissue signal is found, the catheter can be maintained in its position for subsequent ablation. Energy can be delivered through the same electrodes that recorded the aberrant signals, and the ablation can be performed immediately without risk of losing the position of the aberrant signals.

To achieve this functionality with minimal modifications to present ablation and mapping systems, an adapter can be placed between a catheter connector and the cable connector (or between the cable connector and the system), where all or some of the electrical channels used for end effector mapping electrodes can be shorted together to form one or more groups of electrodes which can collective function as together with a larger effective area for ablation. Energy (RF or IRE) can then be delivered—either through the existing cable or system, or through a dedicated cable or system that routes to the adaptor. The catheter can have a high density of electrodes sufficient to achieve desired mapping resolution and a large enough effective electrode contact surface area when the electrical channels are shorted to effectively provide ablation energy to tissue. A physical switch can be placed on the adaptor, where a user can switch between open and shorted states. Or a switch can be available on a user interface of an external computing device such as a graphical user interface (GUI) of a mapping and ablation system. Alternatively, adapter circuitry described herein can be integrated into a handle of a catheter and/or a mapping and ablation system by standard engineering practices, which may become preferable over the adapter if treatments utilizing mapping and ablation techniques described herein become prevalent.

Various shorted patterns can be devised to take advantage of the various form factors of current legacy or future catheter end effectors. Example end effectors illustrated herein include eight radial spines (FIG. 5), five radial spines (FIG. 6), six approximately planar spines joined to form three loop members (FIG. 7), a basket with curved spines (FIG. 8), a circular lasso (FIG. 9) and a linear geometry (FIG. 10). Such end effectors allow for shoring patterns that are too numerous to describe in detail herein; alternative patterns apparent to a person skilled in the pertinent art according to the teachings herein not explicitly listed or described herein are within the scope of the present invention. Further, alternative end effector geometries apparent to a person skilled in the pertinent art according to the teachings herein not explicitly listed or described herein, including those end effectors yet to be developed, are within the scope of the present invention.

General geometries of shorting patterns likely of most use during treatments include localized area, large area, circular, linear, and symmetric groupings. Shorting patterns may be adjusted as clinically required for the targeted arrhythmia/ablation lesion strategy or energy modality. For example, ablation electrode configuration may be optimized for a circular lesion, linear lesion, or focal point ablation (as applicable to pulmonary vein isolation, cavotricuspid isthmus line, or microreentrant circuit). Alternatively, the ablation electrode may be configured to allow for the ideal energy dose to be applied to the tissue (for example higher wattage/voltage).

Shorting patterns can also be selected to select an effective surface area of the shorted electrodes. Electrode surface area affects current density at the electrode/tissue interface. A lower current density can allow a user to apply a higher power/current RF lesion without increasing the risk of steam pop. A larger surface area can also impact the voltage/pulse waveform able to be sustained in an IRE waveform.

FIG. 1 is an illustration of an example portable adapter 100 containing circuitry to toggle between a mapping state and an ablation state so that a catheter can function both as a mapping catheter and an ablation catheter. The adapter 100 includes a first, catheter connector 120, a second, mapping system connector 130, and a third, ablation generator connector 140. The adapter 100 can have a body 102 that is portable so that the adapter 100 can be used with various types of catheters, mapping systems, and ablation systems. The portable body 102 can provide structural support for the connectors 120, 130, 140, circuitry, and other adapter components.

The adapter 100 is also illustrated including a user interface 104 in the form of a mechanical switch to toggle the circuitry between the mapping state and the ablation state. The user interface 104 can have a variety of alternative form factors (buttons, touch screens, knobs, etc.) comparable to user interfaces on known electronic devices. Additionally, or alternatively, the adapter 100 can include a communication system configured to receive instructions from an external computing device and cause the circuitry to toggle between the mapping state and the ablation state. The external device can be external to the body 102 of the adapter 100. For instance, the communication system can include a wireless transmitter configured to respond to wireless transmissions from a computing system or device which may or may not be integral to the mapping system and/or the ablation generator. As another alternative, the adapter can include a wired connection between the communication system of the adapter 100 and the mapping system and/or a wired connection between the communication system of the adapter 100 and the ablation generator.

FIG. 2A is an illustration of an end view of the catheter connector 120. The catheter connector 120 can be configured to mate with a handle of a catheter and can include contacts 124 configured to electrically connect to electrodes on an end effector of the catheter and potentially other catheter electronics such as thermal sensors, navigation sensors, force sensors, etc. The catheter connector 120 can further include a key feature 122 so that the catheter connector 120 is unable to mate with the mapping system and is unable to mate with the ablation generator.

FIG. 2B is an illustration of an end view of the mapping system connector 130. The mapping system connector 130 can be configured to mate with a mapping system. The mapping system connector 130 includes contacts 134 which electrically connect through adapter circuitry with the contacts 124 of the catheter connector 120 when the circuitry of the adapter 100 is in the mapping state. The mapping system connector 130 can further include one or more adapter communication contacts 136. The adapter communication contacts 136 can provide a communication link between the mapping system and the adapter 100. Preferably contacts 134 to the electrodes of the end effector of the catheter electrically isolate the end effector electrodes from each other at the mapping system connector 130. The mapping system connector 130 can further include a key feature 132 so that the mapping system connector 130 is unable to mate with the catheter and is unable to mate with the ablation generator.

FIG. 2C is an illustration of an end view of the ablation generator connector 140. The ablation generator connector 140 can be configured to mate with an ablation generator. The ablation generator connector 140 includes contacts 144 which electrically connect through circuitry of the adapter with the contacts 124 of the catheter connector 120 when the circuitry of the adapter 100 is in the ablation state. Preferably contacts 144 to the electrodes of the end effector of the catheter are shorted together in groups at the ablation generator connector 140. As a result, the ablation generator connector 140 can have fewer contacts 144 to the end effector electrodes compared to the contacts 124 of the catheter connector 120 to the end effector electrodes. The ablation generator connector 140 can further include one or more adapter communication contacts 146. The adapter communication contacts 146 can provide a communication link between the ablation generator and the adapter 100. The ablation generator connector 140 can further include a key feature 142 so that the ablation generator connector 140 is unable to mate with the catheter and is unable to mate with the mapping system.

FIG. 3 is an illustration of an example system 10 configured to map and ablate with a singular catheter 200. The catheter 200 includes an end effector 215 at a distal end of an elongated shaft 212. A control handle 216 at a proximal end of the shaft 212 can be configured to manipulate the catheter 200 and position the end effector 215 against tissue of a treatment site within a patient, e.g. within a blood vessel or a heart. The control handle 216 can further include an irrigation port 265 to provide irrigation fluid to the end effector 215. The control handle 216 can include a control handle connector 204 configured to mate with the catheter connector 120 of the adapter 100.

The system 10 as illustrated includes an integrated mapping and ablation console 40. A suitable integrated mapping and ablation console 40 is, for instance, the CARTO 3 developed by Biosense Webster in California, U.S.A. which allows physicians to visualize the catheter end effector in a three-dimensional virtual model of the heart.

As illustrated in FIG. 3, the integrated mapping and ablation console 40 includes a mapping system port 70 including three connector receptacles 72, 74, 76 and an ablation generator port 69 including a single receptacle. The CARTO 3 system includes multiple mapping system connector receptacles 72, 74, 76 to accommodate a variety of catheters with differing numbers of end effector electrodes, i.e. a catheter having a greater number of end effector electrodes can utilize more mapping system receptacles. The system 10 includes a cable assembly 300 configured to mate the catheter 200 to the mapping system port 70. The cable assembly 300 includes an adapter/catheter connector 302 configured to mate with the adapter 100 and breakout cables 310 to multiple mapping system connectors 312, 322, 332 which can be plugged into corresponding receptacles 72, 74, 76 of the mapping system port 70. The cable assembly 300 can be modified to include more or fewer breakout cables 310 depending on the number of end effector electrodes of the catheter 200. The ablation generator connector 140 of the adapter 100 can be configured to mate directly with the ablation generator port 69 of the integrated mapping and ablation console 20 or indirectly through an extension cable.

Figure 4:
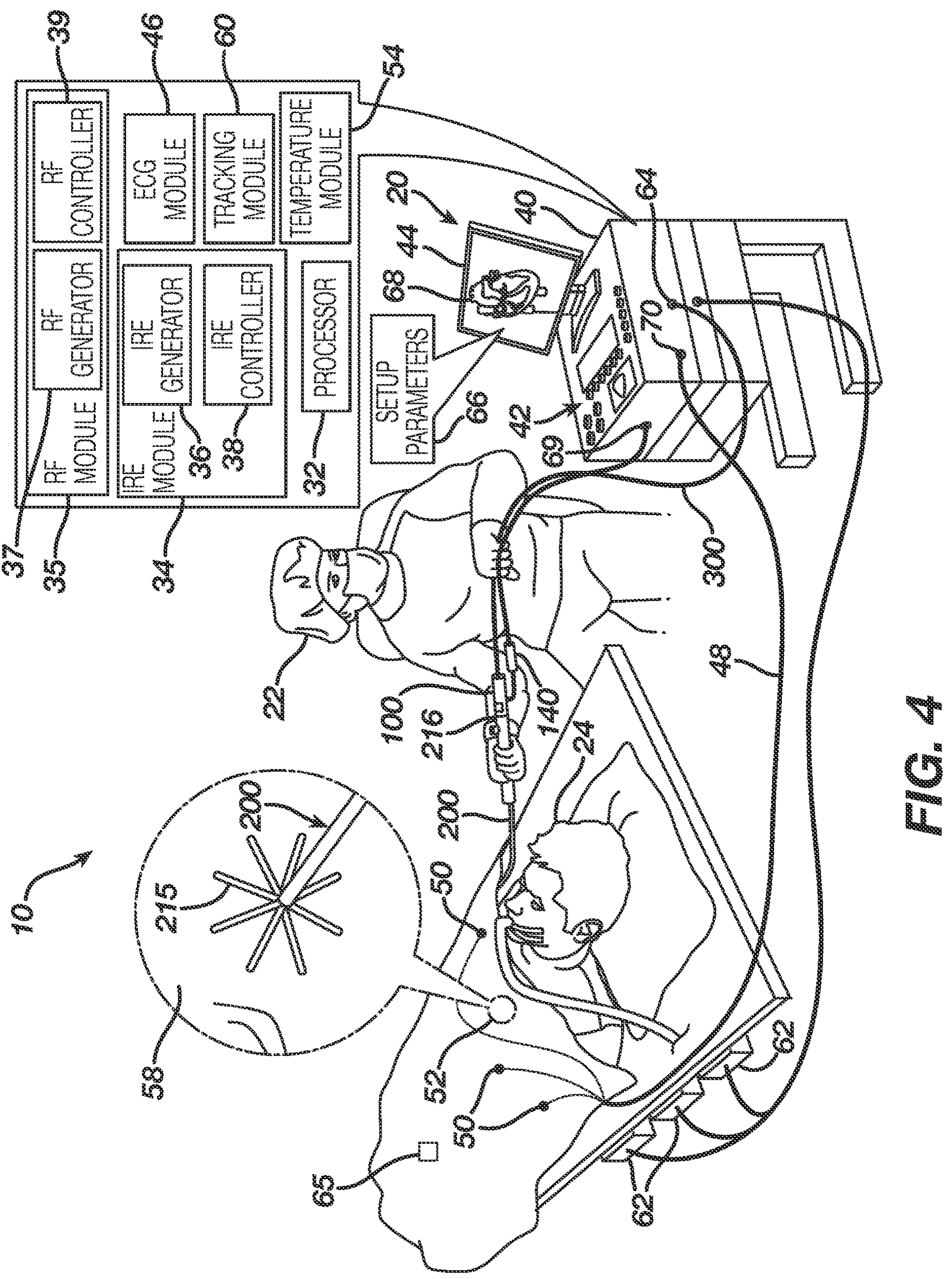
FIG. 4 is an illustration of the example system in use during a treatment according to aspects of the present invention.

FIG. 4 is an illustration of the example system 10 in use during a treatment. The console 40 is illustrated having a larger form factor, although the same principles apply. The console 40 is connected as part of a mapping and ablation system 20 that includes a user interface 42 and a display 44 on which a virtual image of a heart 68 and end effector 215 are displayed. The adapter 100 is illustrated connected directly to a proximal end of the catheter handle 216 with two cables extending respectively to the ablation generator port 69 and the mapping system port 70 of the console 40. Alternatively, the adapter 100 can be configured to be connected directly to the console 40 or circuitry of the adapter 100 can be integrated into the console 40.

To begin the procedure, the physician 22 puts the adapter circuitry into the mapping state by manipulating the user interface 104 of the adapter 100. The physician 22 inserts the catheter 200 into a subject 24, and then navigates the catheter 200, using the control handle 216, to an appropriate site within, or external to, a heart 52. Subsequently, the physician 22 brings some or all of the electrodes of the end effector 215 into contact with tissue 58, such as myocardial or epicardial tissue, of the heart 52. Signals from the electrodes of the end effector 215 are transmitted through the adapter 100 to the mapping system port 70 to detect electrical activity of the heart 52. An indication of the electrical activity is presented on the display 44. When an aberrant signal is detected, the physician 22 puts the adapter circuitry into the ablation state by manipulating the user interface 104 of the adapter 100. The physician 22 can manipulate the user interface 42 of the mapping and ablation system 20 to provide ablation setup parameters 66. The physician 22 may be able to select a pattern of electrodes to apply ablation energy and/or features of electrical signals to apply ablation energy. Finally, the electrical signals can be provided from the ablation generator port 69 of the console 40, through the adapter 100, through the end effector 215, and into tissue 58, thereby ablating the tissue 58. Detection of the aberrant signal and ablation can be performed without moving the end effector 215 with respect to the tissue 58 between the detection and ablation steps.

The illustrated ablation system 20 includes a processor 32, an IRE module 34, an RF module 35, an electrocardiogram (ECG) module 46, a tracking module 60, and a temperature module 54. The modules 34, 35, 46, 60, 54 can, collectively or individually, include non-transitory memory with instructions thereon that can be executed by the processor to perform various functions including those described herein and those understood by a person skilled in the pertinent art according to the teachings herein. The console 40 need not include every module when such module is not necessary for an example treatment. For instance, the system 10 can be adapted for IRE ablation, RF ablation, or both.

The IRE module includes an IRE generator 36 and an IRE controller 38. The RF module 35 includes an RF generator 37 and an RF controller 39. The RF controller 39 and IRE controller 38 can be integral or configured to work in concert. IRE pulses, alone or in combination with RF ablation, can be generated and applied in various treatments such as described in U.S. Patent Pub. No. 2021/0169550, U.S. Patent Pub. No 2021/0169567, U.S. Patent Pub. No. 2021/0169568, U.S. Patent Application No. 62/949,999, U.S. Patent Pub. No. 2021/0161592, U.S. patent application Ser. Nos. 16/731,238, 16/710,062, and U.S. Patent Pub. No. 2021/0186604 incorporated herein by reference and attached in the Appendix of priority U.S. Provisional Patent Application No. 63/220,269. U.S. patent application Ser. No. 16/989,445 claims priority to U.S. 62/949,999 and is published as U.S. Patent Pub. No. 2021/0191642 which is incorporated herein by reference. U.S. patent application Ser. No. 16/731,238 is published as U.S. Patent Pub. No. 2021/0196372 which is incorporated herein by reference. U.S. patent application Ser. No. 16/710,062 is published as U.S. Patent Pub. No. 2021/0177503 which is incorporated herein by reference.

In response to receiving the setup parameters 66, the processor 32 communicates these parameters to the IRE controller 38 and/or RF controller 39, which commands the IRE generator 36 and/or RF generator 37 to generate IRE signals and/or RF signals in accordance with the setup requested by physician 22. Additionally, the processor 32 may display setup parameters 66 on display screen 44.

The RF module 35 and IRE module 34 are illustrated as separate modules for the sake of illustration, and it is to be understood that the modules can share common hardware and software components. The processor 32, IRE controller 38, and RF controller 39 each can include a programmable processor, which is programmed in software and/or firmware to carry out the functions that are described herein. Alternatively, or additionally, the IRE controller 38, RF controller 39, and/or processor 32 can each include hard-wired and/or programmable hardware logic circuits, which carry out at least some of these functions. Although the processor 32 is illustrated as a functional block separate from the IRE controller 38 and RF controller 39, in practice some of these functions may be combined in a single processing and control unit, with suitable interfaces for receiving and outputting the signals that are illustrated in the figures and are described in the text. For instance, the IRE controller 38 can reside within the IRE module 34, as high-speed control signals are transmitted from the IRE controller to the IRE generator 36. However, provided that signals at sufficiently high speeds may be transmitted from the processor 32 to the IRE generator 36, the IRE controller 38 can reside within the processor.

The processor 32 and the IRE module 34 can reside within the console 40. The electrocardiogram (ECG) module 46, the temperature module 54, and/or the tracking module 60 can reside within the console 40 and can be connected to suitable interfaces and devices in the system 20. As illustrated, the electrocardiogram (ECG) module 46 is coupled through a cable 48 to ECG electrodes 50, which are attached to the subject 24. The ECG module 46 is configured to measure the electrical activity of a heart 52 of the subject 24.

The temperature module 54 is coupled to optional temperature sensors (not illustrated) in a distal portion of the catheter 200. The temperature module 54 can be connected to the mapping system port 70 which can be connected to one or more of the connectors 134 of the mapping system connector 130 of the adapter 100 when the circuitry of the adapter 100 is in the mapping state to thereby receive signals for the temperature sensors in the catheter 200. Additionally, or alternatively, the temperature module 54 can be connected to the ablation generator port 69 which can be connected to one or more of the contacts 144 of the ablation generator connector 140 of the adapter 100 when the circuitry of the adapter 100 is in the ablation state to thereby receive signals for the temperature sensors in the catheter 200.

The tracking module 60 is coupled to one or more electromagnetic position sensors (not illustrated) in a distal portion of the catheter 200. In the presence of an external magnetic field generated by one or more magnetic field generators 62, the electromagnetic position sensors output signals that vary with the positions of the sensors. Based on these signals, the tracking module 60 may ascertain the positions of the end effector 215 in the heart 52. The tracking module 60 can be connected to the electromagnetic position sensors in the catheter 200 via the mapping system port 70 and via one or more of the connectors 134 of the mapping system connector 130 of the adapter 100 when the circuitry of the adapter 100 is in the mapping state. Additionally, or alternatively, the tracking module 60 can be connected to the electromagnetic position sensors in the catheter 200 via the ablation generator port 69 and via one or more of the contacts 144 of the ablation generator connector 140 of the adapter 100 when the circuitry of the adapter 100 is in the ablation state.

The modules 46, 54, 60 typically include both analog and digital components, and are configured to receive analog signals and transmit digital signals. Each module can additionally include hard-wired and/or programmable hardware logic circuits, which carry out at least some of the functions of the module.

One or more external electrodes 65, or "return patches", can be coupled externally to the subject 24, typically on the skin of the subject's torso and the console 40 (not illustrated). The return patch(es) 65 can provide a return path (return paths) for unipolar ablation signals applied at one or more of the electrodes of the end effector 215. RF ablation and IRE ablation can each be applied in a unipolar ablation scheme. Further, RF ablation and IRE ablation can each be applied in a bipolar ablation scheme. Presently it is more common for RF ablation to be performed in a unipolar ablation scheme and for IRE to be performed in a bipolar ablation scheme. The example catheter 200 and the example system 10 can be adapted to perform unipolar RF ablation, unipolar IRE ablation, bipolar RF ablation, unipolar IRE ablation, or any combination thereof.

During unipolar RF ablation, RF energy is delivered from shorted electrodes of the end effector 215 to the return patch 65. The electrical alternating current flowing through the tissue encounters resistance, and the energy is converted into heat. This energy, resistive heat, destroys the tissue close to the activated catheter electrode(s). Heat is then transmitted to the surrounding tissue by conduction and radiation leading to lesion formation. Scar formation is related to the electrode size, power of the energy, the contact force between the electrode and the tissue and the cooling effect of the surrounding fluid, even though only a small amount of the energy is delivered to the tissue. Cooling the electrode can reduce the risk of overheating the tissue thereby enabling creation of a deeper lesion. The system 10 can include irrigation (not illustrated) as understood by a person skilled in the pertinent art. Decrease of distance between the electrode of the end effector 215 and the return patch 65 can result in a bigger current density with more resistive heating, which leads to deeper lesion formation. Bipolar RF ablation is when RF current flows between two of the catheter electrodes. Lesions created by bipolar RF ablation are generally narrower and deeper than lesions created by unipolar RF ablation, resulting in a transmural scar in the tissue as thick as about 25 mm.

During bipolar IRE ablation, biphasic pulses are applied between catheter electrodes (typically in pairs) to create an electric field between the electrodes. Cells at and between the electrodes experience the greatest electric fields and undergo electroporation. During unipolar IRE ablation, biphasic pulses are applied between shorted catheter electrodes and the return patch(es) 65 to create an electric field between the end effector 215 and the return patch(es) 65.

The processor 32 is configured to receive setup parameters 66 from the physician 22 or another user or device. Using one or more suitable input devices 42, the physician 22 can input the parameters of ablation signals for RF ablation and/or IRE ablation. The end effector electrodes can be shorted together in groups by the circuitry of the adapter in the mapping state so that the groups can be activated individually from each other during ablation. The physician 22 may select groups of shorted end effector electrodes for activation (for receiving the IRE pulses and/or RF signals) and the order in which they are activated. In setting up the ablation, the physician 22 may also choose a mode of synchronization of the IRE pulses with respect to the cycle of heart 52.

Figure 5:
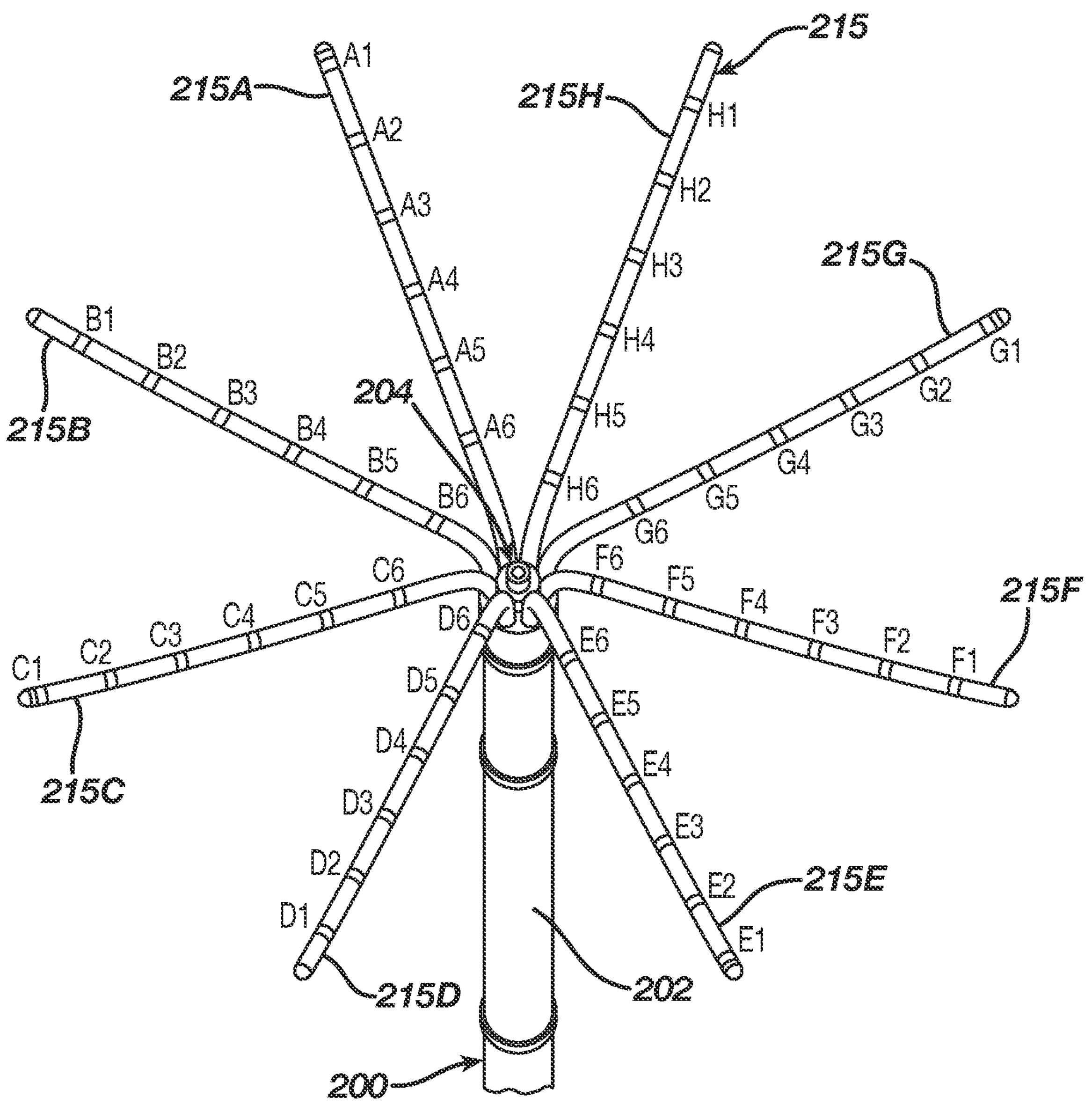
FIG. 5 is an illustration of an example end effector of a catheter according to aspects of the present invention.

FIG. 5 is an illustration of a distal portion of an example catheter 200. The catheter includes a shaft 212 that is elongated to navigate the catheter 200 through vasculature and an end effector 215 on the distal end of the shaft 212. The end effector includes eight spines 215A-H. The spines are illustrated in an expanded configuration shaped to be pressed against tissue 58 as illustrated in FIG. 4. The spines 215A-H extend radially from the shaft 212. The spines 215A-H can be contracted together so that the end effector 215 can be navigated through vasculature. The end effector 215 can further include an irrigation port 206 configured to irrigate the tissue 58 in the vicinity of the electrodes.

Each spine includes electrodes A1-6, B1-6, C1-6, D1-6, E1-6, F1-6, G1-6, H1-6 distributed along the respective spine 215A-H. As illustrated, the end effector 215 includes six electrodes per spine on eight spines. The end effector 215 can be modified to include alternative numbers of spines and electrodes per spine as understood by a person skilled in the pertinent art.

The electrodes can be distributed to detect electrical signals through the tissue 58. Some or all of the electrodes can be shorted together in one or more groups by the adapter 100 when the circuitry is in the ablation state. In one example all forty-eight electrodes can be shorted together for a single, large-tip ablation. In another example, the eight innermost electrodes A6, B6, C6, D6, E6, F6, G6, H6 can be shorted together for a smaller zone of ablation. The remaining electrodes can be shorted together in groups to form concentric rings. In another example, the spines 215A-H can be subdivided into four sectors, where the twelve electrodes from a first pair of adjacent spines 215A, 215B are shorted together to form a first sector, twelve electrodes from a second pair of adjacent spines 215C, 215D are shorted together to form a second sector, twelve electrodes from a third pair of adjacent spines 215E, 215F are shorted together to form a third sector, and twelve electrodes from a fourth pair of adjacent spines 215G, 215H are shorted together to form a fourth sector. In the embodiments described herein, the minimum surface area for one electrode (or a group of electrode) to effectively ablate using pulsed field (direct current) bipolar ablation (IRE) is believed to be approximately 6 millimeters squared.

Figure 6:
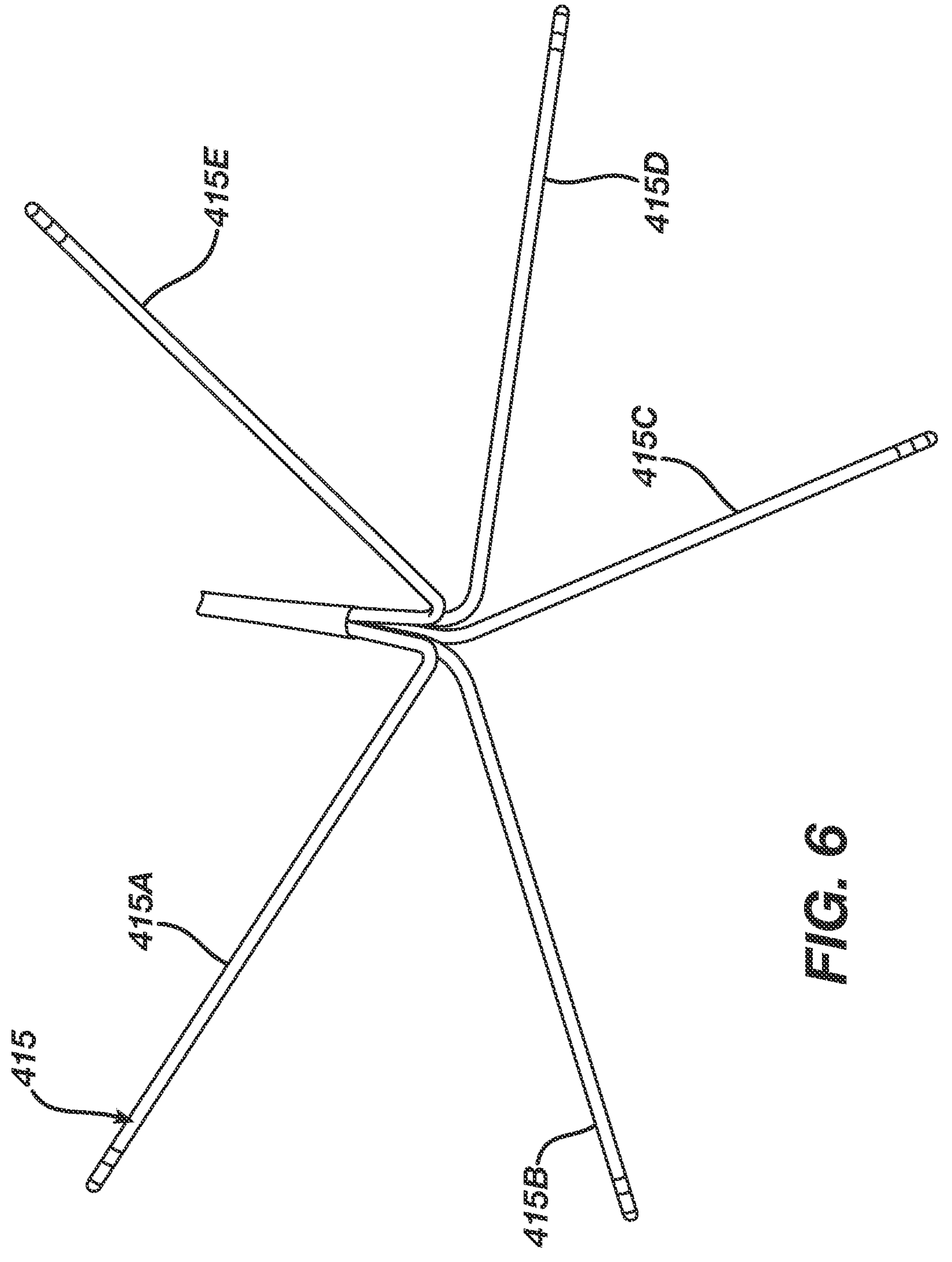
FIG. 6 is an illustration of another example end effector of a catheter according to aspects of the present invention.

FIG. 6 is an illustration of another example end effector 415 having five spines 415A-E. The spines can carry electrodes that can be shorted in a manner similar to that of the end effector having eight spines 215A-H illustrated in FIG. 5. The catheter can otherwise be configured similarly to as described in U.S. Pat. No. 7,228,164 incorporated herein by reference and attached in the Appendix of priority U.S. Provisional Patent Application No. 63/220,269.

Figure 7:
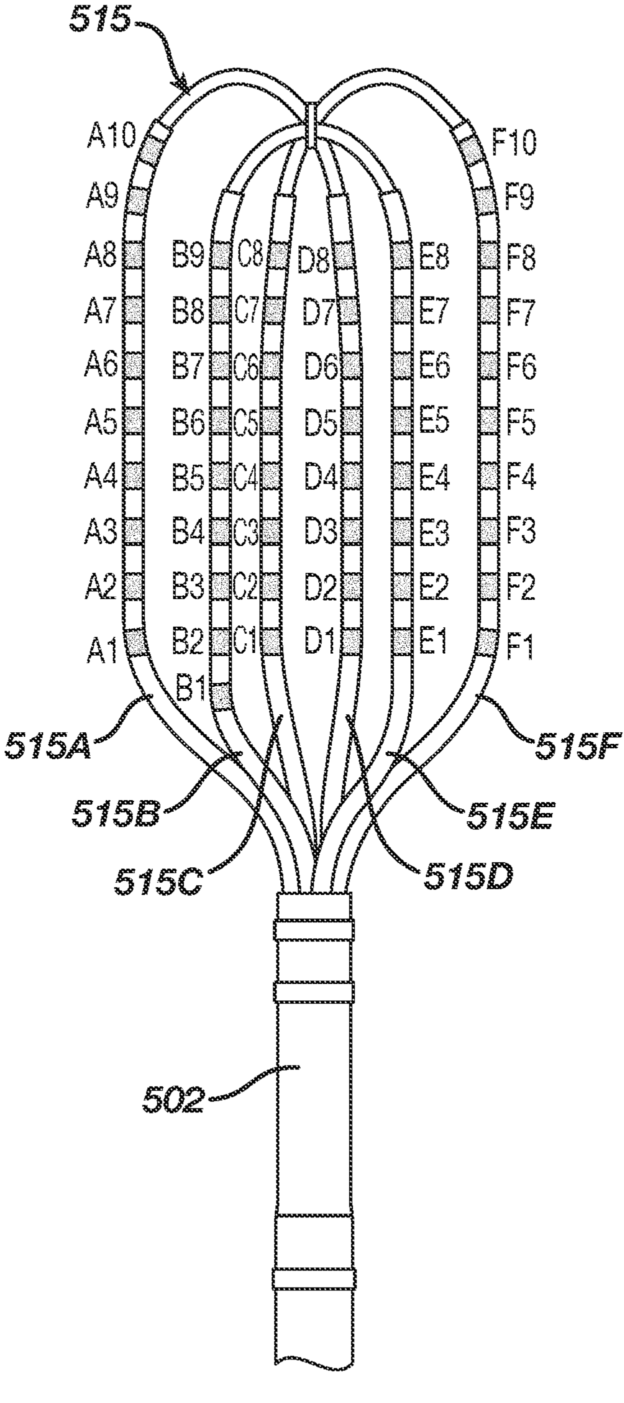
FIG. 7 is an illustration of another example end effector of a catheter according to aspects of the present invention.

FIG. 7 is an illustration of another example end effector 515 at a distal end of a shaft 502 of another example catheter. The end effector 515 includes six spines 515A-F arranged generally parallel to each other. The spines 515A-F are approximately planar but for overlap of segments at a distal end of the end effector 515 and proximal end of the end effector 515. The end effector 515 includes outer spines 515A, 515F each having ten electrodes A1-10, F1-10 apiece. The end effector includes three inner spines 515C-E having eight electrodes C1-8, D1-8, E1-8 apiece. The end effector 515 includes an inner spine 515B having nine electrodes B1-9. The end effector 515 can be modified to include alternative numbers of spines and electrodes per spine as understood by a person skilled in the pertinent art. The end effector 515 can be otherwise be configured similarly to as described in U.S. patent application Ser. No. 17/029,890 incorporated herein by reference and attached in the Appendix of priority U.S. Provisional Patent Application No. 63/220,269. U.S. patent application Ser. No. 17/029,890 is published as U.S. Patent Publication No. 2021/0369132, incorporated herein by reference.

The electrodes can be distributed to detect electrical signals through the tissue 58. The electrodes can be shorted together to form various geometrical patterns when the circuitry is in the mapping state. All electrodes can be shorted together for a single, large-tip ablation catheter. Alternatively, the flat plane can be subdivided into halves, quarters, sixths, etc.

Figure 8:
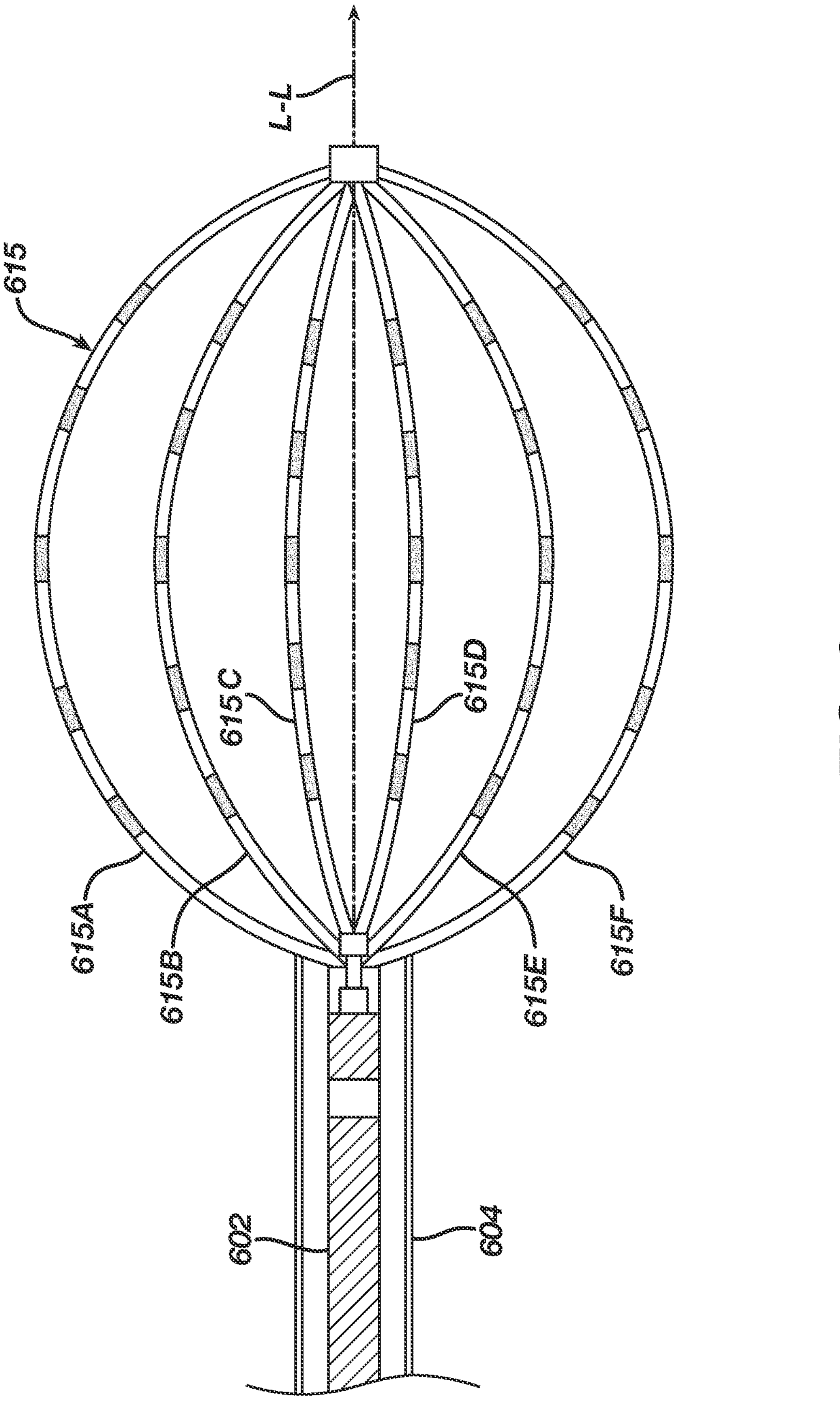
FIG. 8 is an illustration of another example end effector of a catheter according to aspects of the present invention.

FIG. 8 is an illustration of another example end effector 615 at a distal end of a shaft 602 of a catheter. The end effector 615 is illustrated in an expanded basket shape and can be contracted into a delivery tube 604 to be delivered through vasculature. The end effector 615 includes eight curved spines 615A-F having electrodes thereon arranged in a three-dimensional array. The catheter can otherwise be configured similarly to as described in U.S. Patent Publication 2020/0206461 incorporated herein by reference and attached in the Appendix of priority U.S. Provisional Patent Application No. 63/220,269.

The electrodes can be distributed to detect electrical signals through the tissue 58. All the electrodes can be shorted together for a single, large-tip ablation catheter. Alternatively, all electrodes along a certain spherical latitude can be shorted for a circumferential lesion. A certain quadrant can be shorted together for a focal or small linear lesion with parallel tissue contact.

Figure 9:
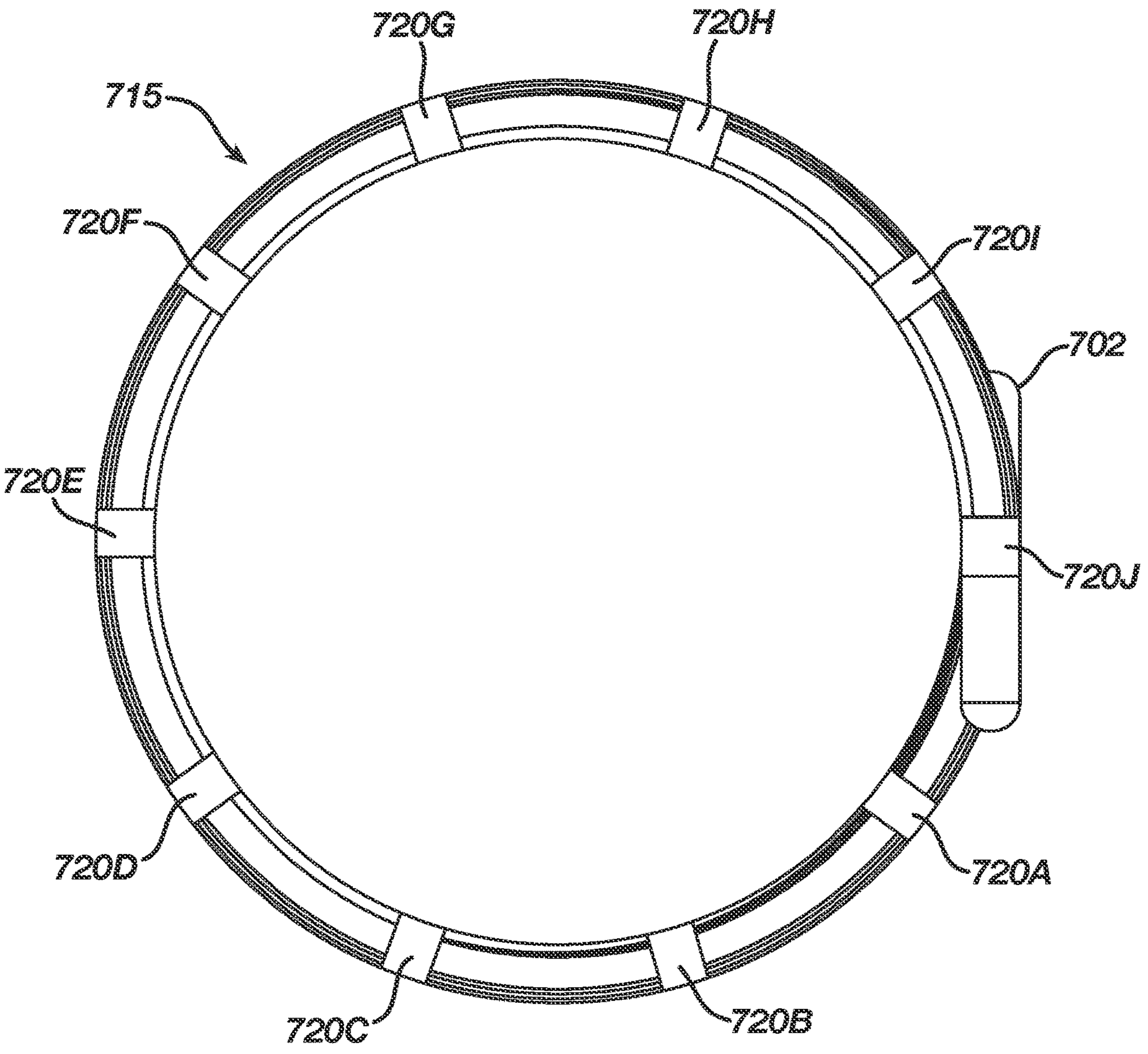
FIG. 9 is an illustration of another example end effector of a catheter according to aspects of the present invention.
Figure 10:
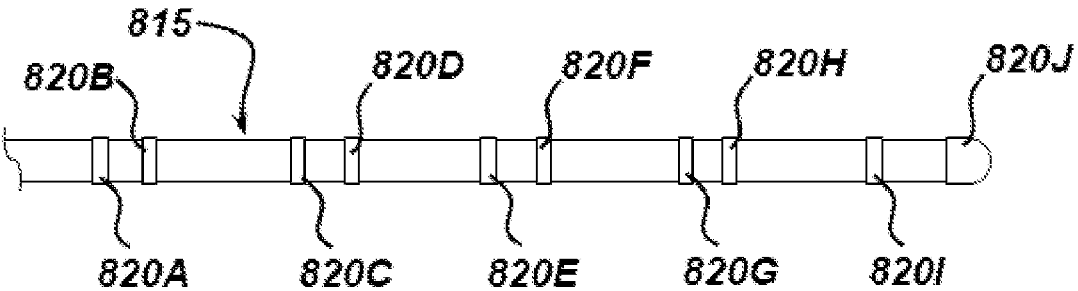
FIG. 10 is an illustration of another example end effector of a catheter according to aspects of the present invention.

FIG. 9 is an illustration of another example end effector 715 of a catheter. The end effector 715 has a circular shape having ten electrodes 720A-J distributed around the perimeter of the circular shape. The catheter can otherwise be configured similarly to as described in U.S. Pat. No. 6,987,995 incorporated herein by reference and attached in the Appendix of priority U.S. Provisional Patent Application No. 63/220,269. For example, the catheter can have between about 6 and about 20 electrodes.

The electrodes can be distributed to detect electrical signals through the tissue 58. All the electrodes can be shorted together for a single, large-tip ablation catheter. Quadrants, hemispheres, or simple pairs of electrodes could be shorted together and would result in different electrode configurations/geometries for IRE. Shorting across the diameter of the circle may also be useful for 'debulking' ablation strategies, or large isolation targets like the posterior wall, in a safer manifestation of an RF single-tip ablation catheter.

FIG. 10 is an illustration of another example end effector 815 of a catheter. The end effector 815 has a linear shape having ten ring electrode 820A-J distributed linearly and including a tip electrode 820J. The electrodes can be distributed to detect electrical signals through the tissue 58. All the electrodes can be shorted together for a single, large-tip ablation catheter. Alternatively, sub-groupings of the electrodes can be shorted together to achieve RF and/or IRE ablation.

Figure 11:
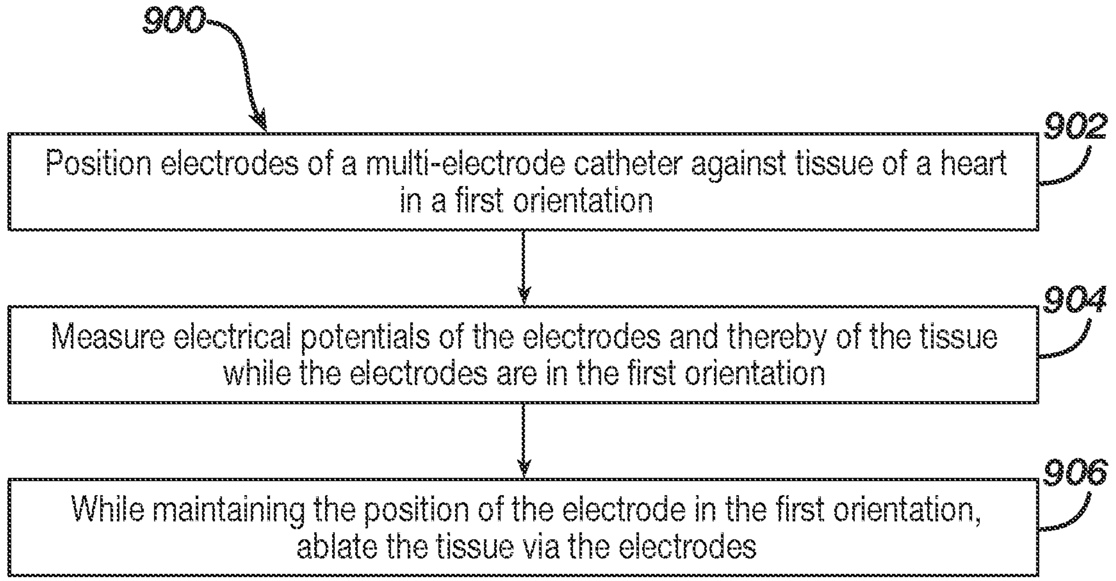
FIG. 11 is an illustration of a flow diagram of an example method of treatment according to aspects of the present invention.

FIG. 11 is an illustration of a flow diagram of an example method 900 of treatment. The method 900 can be carried out with the adapter 100 and/or system 10 disclosed herein, variations thereof, and alternatives thereto as understood by a person skilled in the pertinent art according to the teachings herein. At step 902, electrodes of a multi-electrode catheter can be positioned against tissue of a heart in a first orientation. At step 904, electrical potentials of the electrodes, and thereby of the tissue, can be measured while the electrodes are in the first orientation. At step 906, the tissue can be ablated via the electrodes while maintaining the position of the electrodes in the first orientation.

What is claimed is:

1. A method of treating cardiac arrhythmia comprising:

joining a first plurality of contacts of a first connector of an adapter to a multi-electrode catheter such that a plurality of electrodes of the multi-electrode catheter are in electrical communication with the first plurality of contacts, the adapter being configured to toggle between a mapping state and an ablation state;

joining a second plurality of contacts of a second connector of the adapter to a mapping system configured to measure electrical potentials of the plurality of electrodes, the first plurality of contacts being in electrical communication with the second plurality of contacts in the mapping state such that the first plurality of contacts are electrically isolated from each other;

joining a third plurality of contacts of a third connector of the adapter to an ablation generator configured to deliver ablative energy to tissue via the plurality of electrodes, the third connector being different from the second connector and the third plurality of contacts being different from the second plurality of contacts, the first plurality of contacts being in electrical communication with the third plurality of contacts in the ablation state such that:

a first portion of the first plurality of contacts are electrically shorted to each other via the adapter, a second portion of the first plurality of contacts are electrically shorted to each other via the adapter, and the first portion is electrically isolated from the second portion;

positioning at least a portion of the plurality of electrodes of the multi-electrode catheter against tissue of a heart in a first orientation;

measuring electrical potentials of the plurality of electrodes and thereby of the tissue of the heart while the at least a portion of the plurality of electrodes are in the first orientation; and while maintaining the position of the at least a portion of the plurality of electrodes in the first orientation, toggling the adapter via a user interface from the mapping state to the ablation state and ablating the tissue of the heart via the at least a portion of the plurality of electrodes.

2. The method of claim 1, further comprising:

measuring the electrical potentials of additional electrodes of the multi-electrode catheter; and deactivating the additional electrodes while ablating the tissue of the heart.

3. The method of claim 1, wherein measuring the electrical potentials of the plurality of electrodes comprises measuring electrical potentials between first and second electrodes of the plurality of electrodes, and wherein ablating the tissue of the heart comprises synchronously applying an electrical signal to the first and second electrodes of the plurality of electrodes.

4. The method of claim 3, further comprising:

positioning the first and second electrodes of the plurality of electrodes such that the first and second electrodes of the plurality of electrodes are on a common spine of the multi-electrode catheter.

5. The method of claim 3, further comprising:

positioning the first and second electrodes of the plurality of electrodes such that the first electrode of the plurality of electrodes is on a first spine of the multi-electrode catheter and the second electrode of the plurality of electrodes is on a second spine of the multi-electrode catheter distinct from the first spine.

6. The method of claim 1, wherein measuring the electrical potentials of the plurality of electrodes comprises measuring a distinct electrical potential at each electrode of the plurality of electrodes, and wherein ablating the tissue of the heart comprises applying a first electrical signal to the first portion of the plurality of electrodes that are electrically shorted to each other and applying a second electrical signal distinct from the first electrical signal to the second portion of the plurality of electrodes that are electrically shorted to each other.

7. The method of claim 1, further comprising:

applying radio frequency (RF) electrical energy from the plurality of electrodes to the tissue of the heart thereby thermally ablating the tissue of the heart.

8. The method of claim 1, further comprising:

applying voltage pulses to the plurality of electrodes thereby ablating the tissue of the heart with irreversible electroporation, such that a cumulative electrode surface area of the plurality of electrodes is at least a minimum electrode surface area required for irreversible electroporation ablation.

9. The method of claim 1, further comprising:

wherein toggling the plurality of electrodes via the user interface comprises moving a mechanical switch on the adapter.

10. The method of claim 1, further comprising a communication system, the method further comprising:

transmitting instructions from an external computing system to the communication system of the adapter to cause the multi-electrode catheter to toggle between measuring the electrical potentials of the plurality of electrodes and ablating the tissue via the plurality of electrodes, the external computing system being external to a portable body of the adapter.

11. The method of claim 10, the communication system comprising a wireless transmitter configured to receive wireless transmission, wherein transmitting instructions from the external computing system to the communication system of the adapter comprises transmitting the instructions wirelessly to the wireless transmitter.

12. The method of claim 1, wherein the first plurality of contacts comprises an equal number of contacts as the second plurality of contacts and a greater number of contacts than the third plurality of contacts.

* * * * *